United States Patent
Magnani et al.

(10) Patent No.: US 10,619,208 B2
(45) Date of Patent: Apr. 14, 2020

(54) METHOD OF EVALUATING THE RESPONSE OF ATAXIA TELANGIECTASIA PATIENTS TO GLUCOCORTICOIDS TREATMENT

(71) Applicant: EryDel S.p.A., Urbino (IT)

(72) Inventors: Mauro Magnani, Urbino (IT); Sara Biagiotti, Tavullia (IT); Michele Menotta, Fano (IT)

(73) Assignee: EryDel S.p.A., Urbino (IT)

( * ) Notice: Subject to any disclaimer, the term of this patent is extended or adjusted under 35 U.S.C. 154(b) by 0 days.

(21) Appl. No.: 15/544,487

(22) PCT Filed: Jan. 19, 2016

(86) PCT No.: PCT/IB2016/050238
§ 371 (c)(1),
(2) Date: Jul. 18, 2017

(87) PCT Pub. No.: WO2016/116850
PCT Pub. Date: Jul. 28, 2016

(65) Prior Publication Data
US 2018/0016637 A1 Jan. 18, 2018

(30) Foreign Application Priority Data
Jan. 19, 2015 (IT) .............................. RM2015A0022

(51) Int. Cl.
C12Q 1/68 (2018.01)
C07H 21/04 (2006.01)
C12Q 1/6883 (2018.01)
C12Q 1/6806 (2018.01)

(52) U.S. Cl.
CPC ......... *C12Q 1/6883* (2013.01); *C12Q 1/6806* (2013.01); *C12Q 2600/142* (2013.01); *C12Q 2600/156* (2013.01); *C12Q 2600/158* (2013.01)

(58) Field of Classification Search
None
See application file for complete search history.

(56) References Cited

PUBLICATIONS

Biagiotti et al. (Mol. Cell Biochem, vol. 392, pp. 13-30, 2014) (Year: 2014).*
Menotta et al. J. of Rare Diseases, vol. 12, No. 126, 2017 (Year: 2017).*
Juruena et al. (Psychopharmacology, vol. 189, pp. 225-235, 2006 (Year: 2006).*
Menotta et al. (J. of Biological Chemistry, vol. 287, No. 49, pp. 41352-41363, Nov. 2012) (Year: 2012).*
Biagiotti et al., "Forward subtractive libraries containing genes transactivated by dexamethasome in ataxia-telangiectasia lymphoblastoid cells," Molecular and Cellular Biochemistry, Mar. 14, 2014, pp. 13-30, vol. 392, No. 1, Springer, Norwell, MA.
International Search Report and Written Opinion issued in PCT/IB2016/050238 dated Apr. 28, 2016.
Kuang et al., "Control of ATM-/-thymic lymphoma cell proliferation in vitro and in vivo by dexamethasone," Cancer Chemotherapy and Pharmacology, Nov. 27, 2004, pp. 203-212, vol. 55, No. 3.
Menotta et al., "Dexamethasone Partially Rescues Ataxia Telangiectasia-mutated (ATM) Deficiency in Ataxia Telangiectasia by Promoting a Shortened Protein Variant Retaining Kinase Activity," The Journal of Biological Chemistry, Nov. 30, 2012, pp. 41352-41363, vol. 287, No. 49.
Broccoletti T, Del GE, Amorosi S, Russo I, Di BM et al. "Steroid-induced improvement of neurological signs in ataxia telangiectasia patients." Eur J Neurol 2008, 15:223-228.
Buoni S, Zannolli R, Sorrentino L, and Fois A. "Betamethasone and improvement of neurological symptoms in ataxia-telangiectasia." Arch Neurol 2006, 63:1479-1482.
Russo I, Cosentino C, Del GE, Broccoletti T, Amorosi S et al. "In ataxia-teleangiectasia betamethasone response is inversely correlated to cerebellar atrophy and directly to antioxidative capacity." Eur J Neurol 2009, 16:755-759.
Broccoletti T, Del GE, Cirillo E, Vigliano I, Giardino G et al. "Efficacy of very-low-dose betamethasone on neurological symptoms in ataxia-telangiectasia." Eur J Neurol 2011, 18:564-570.
Gatti RA and Perlman S. "A proposed bailout for A-T patients?" Eur J Neurol 2009, 16:653-655.
Biagiotti S, Paoletti MF, Fraternale A, Rossi L, and Magnani M. "Drug delivery by red blood cells." IUBMB Life 2011, 63:621-631.
Bossa F, Latiano A, Rossi L, Magnani M, Palmieri O et al. "Erythrocyte-mediated delivery of dexamethasone in patients with mild-to-moderate ulcerative colitis, refractory to mesalamine: a randomized, controlled study." Am J Gastroenterol 2008, 103:2509-2516.
Castro M, Rossi L, Papadatou B, Bracci F, Knafelz D et al. "Long-term treatment with autologous red blood cells loaded with dexamethasone 21-phosphate in pediatric patients affected by steroid-dependent Crohn disease." J Pediatr Gastroenterol Nutr 2007, 44:423-426.
Pierige F, Serafini S, Rossi L, and Magnani M. "Cell-based drug delivery." Adv Drug Deliv Rev 2008, 60:286-295.
Rossi L, Serafini S, Cenerini L, Picardi F, Bigi L et al. "Erythrocyte-mediated delivery of dexamethasone in patients with chronic obstructive pulmonary disease." Biotechnol Appl Biochem 2001, 33:85-89.
Chessa L, Leuzzi V, Plebani A, Soresina A, Micheli R et al. "Intra-erythrocyte infusion of dexamethasone reduces neurological symptoms in ataxia teleangiectasia patients: results of a phase 2 trial." Orphanet J Rare Dis 2014, 9:5.

* cited by examiner

*Primary Examiner* — Jeanine A Goldberg
(74) *Attorney, Agent, or Firm* — Arent Fox LLP

(57) ABSTRACT

The present invention relates to a novel procedure for evaluating the response of patients affected by Ataxia Talangiectasia (A-T) to glucocorticoids treatment. In particular, the procedure provides a step of qualitative and/or quantitative identification in the blood of said patients of the expression of a mRNA variant of the ATM (Ataxia-Talangiectasia-Mutated) gene produced by non-canonical splicing induced by glucocorticoid (GC). In fact, it was demonstrated that mRNA variant expression is present in the blood of patients who responded positively to treatment with GC.

13 Claims, 7 Drawing Sheets
Specification includes a Sequence Listing.

a)

|                      |        |         |       |       |
|----------------------|-------:|--------:|------:|------:|
| Number of values     | 3      | 3       | 3     | 3     |
| Mean                 | 4.317  | -0.3333 | 15.69 | 13.33 |
| Standard deviation   | 3.003  | 1.528   | 7.713 | 2.082 |
| Standard error       | 1.734  | 0.8819  | 4.453 | 1.202 |
| Lower 95% CI of mean | -3.142 | -4.128  | -3.470| 8.162 |
| Upper 95% CI of mean | 11.78  | 3.461   | 34.85 | 18.50 |
| Total                | 12.95  | -1.000  | 47.07 | 40.00 |

| 1 mini ATM | 1 ΔICARS | 2 Mini ATM | 2 ΔICARS |
|-----------:|---------:|-----------:|---------:|
| 3.44       | 1.       | 10.95      | 11.      |
| 7.66       | 0.       | 11.53      | 14.      |
| 1.85       | -2.      | 24.59      | 15.      |

Mini ATM    cut-off = 4.3 ± 6

ΔICARS    cut-off= -0.33 ± 3

METHOD OF EVALUATING THE RESPONSE OF ATAXIA TELANGIECTASIA PATIENTS TO GLUCOCORTICOIDS TREATMENT

CROSS-REFERENCE TO RELATED APPLICATIONS

This application is a National Stage entry of International Application No.: PCT/IB2016/050238, filed Jan. 19, 2016, which claims priority to Italian Patent Application No. RM2015A000022, filed Jan. 19, 2015. The disclosure of the priority applications are hereby incorporated in their entirety by reference.

FIELD OF THE INVENTION

The present invention relates to a novel procedure for evaluating the response of patients affected by Ataxia Talangiectasia (A-T) to glucocorticoids treatment. In particular, the procedure provides a step of qualitative and/or quantitative identification in the blood of said patients of the expression of a mRNA variant of the ATM (Ataxia Talangiectasia-Mutated) gene produced by non-canonical splicing induced by glucocorticoid (GC). In fact, it was demonstrated that mRNA variant expression is present in the blood of patients who responded positively to treatment with GC.

STATE OF THE PRIOR ART

In the last years, various clinical trials provided evidences that short-term treatment with glucocorticoids (GC) is able to improve neurological symptoms in A-T patients, and even the state of cerebellar atrophy in some subjects [1-4]. Unfortunately, such an improvement is merely transitory and disappears shortly after discontinuation of oral treatment with GC; discontinuation is necessary, as the hazards of a long-term therapy with steroids would risk to surpass its benefits [5]. On the other hand, the administration of very low GC doses by erythrocytes could reduce steroids toxicity without compromising their effectiveness [6-10]. Therefore, in 2010 a phase II Clinical study was set up which envisaged the long-term treatment of A-T patients by dexamethasone encapsulated within autologous erythrocytes [11]. The proposed therapy brought about a significant improvement in neurological symptoms, concomitantly avoiding the onset of known side effects typical of GC.

Recently, in vitro experiments, conducted on stabilized lymphoblastoid cell lines from lymphocytes of A-T patients, allowed the Inventors to demonstrate that the action of synthetic GC dexamethasone (dexa) action may be exerted through synthesis of a new messenger RNA (mRNA) molecule generated by a non-canonical splicing event in the pre-mRNA precursor of the ATM gene (Ataxia Telangiectasia Mutated gene) [14].

In silico studies suggested that the resulting transcript, referred to by the Inventors as ATMdexa1, instead of being junk RNA, could be translated by cellular mechanisms into a new "shortened" form of the ATM protein, skipping all mutations, present in the gene of AT patients, upstream of the sequence encoding the kinase and functional enzyme domain. This protein variant, named mini-ATM, was effectively identified in the lymphoblastoid cell lines and demonstrated to be potentially active. These findings led the Inventors to hypothesize that dexa treatment may restore, at least partly, the defective ATM protein in Ataxia telangiectasia by means of this novel molecular mechanism that, surprisingly, could allow to "skip" most of the mutations so far described for the ATM gene.

SUMMARY OF THE INVENTION

The present invention is based on the discovery that a new transcript of mRNA variant of the ATM gene (Ataxia-Talagiectasia-Mutated gene) produced by non-canonical splicing induced by glucocorticoids (GC) treatment is identifiable in blood samples obtained from A-T patients subjected to treatment with GC, and that its presence correlates with positive response to therapeutic treatment.

Hence, object of the present patent application is a novel procedure for quantitatively or qualitatively analyzing the mRNA variant of the ATM gene as biomarker of response to glucocorticoids treatment, such as dexamethasone, in the blood of patients. In fact, it was demonstrated by the present inventors that the expression of said mRNA variant is present in the blood of patients that responded positively to GC treatment, above all when the medicament is encapsulated within erythrocytes, but is absent in healthy controls and in patients not receiving the drug.

Hence, objects of the present application are:

A method for evaluating the response of patients affected by Ataxia Talangiectasia to glucocordicoids treatment, comprising a step of qualitative and/or quantitative identification in the blood of said patients of the expression of a mRNA variant of the gene ATM (Ataxia-Talangiectasia-Mutated gene), wherein said mRNA variant is produced by non-canonical splicing induced by glucocorticoid and contains the Phosphatidyl Inositol 3 Kinase domain, and wherein detectable expression values of said mRNA variant indicate positive response to treatment.

A method for treating patients affected by Ataxia Talangiectasia, comprising
- a step of administering an amount of glucocorticoide, preferably dexamethasone, in said patient;
- a step of qualitative and/or quantitative identification in the blood of said patients of the expression of a mRNA variant of the gene ATM (Ataxia-Talangiectasia-Mutated gene) wherein said mRNA variant is produced by non-canonical splicing induced by glucocorticoid and contains the Phosphatidyl Inositol 3 Kinase domain, and wherein detectable expression values of said mRNA variant indicate positive response to treatment;
- a step of adjusting said therapy depending on the response.

In one embodiment of the invention, the glucocorticoid is selected from: prednisolone, dexamethasone, betamethasone, deflazacort, or pharmaceutically acceptable salts thereof.

In another embodiment of the invention, the mRNA variant of the ATM gene is ATMdexa1 mRNA.

In a further embodiment, the identification of the expression of the mRNA variant is quantitative and is normalized against the expression of a housekeeping gene.

In a further embodiment of the invention, the identification of the mRNA variant is performed by any technique of amplification using suitable 5'-3' forward and 5'-3' reverse primer pairs, optionally associated with probes.

In an alternative embodiment of the invention, the glucocorticoide is encapsulated within erythrocytes.

The advantages afforded by the present invention are immediately evident to a person skilled in the art, when considering that the treatment with corticosteroids is often accompanied by adverse effects, even serious ones, above all when the treatment is prolonged over time and/or conducted on a pediatric population. Apparently, the prognostic tool afforded by the present invention avoids the prolonging of treatments in subjects not responding (non-responders) or not sufficiently responding to therapy, and therefore of useless and harmful treatments. Moreover, by measuring ATMdexa1 expression levels it is possible to establish the optimal frequency of glucocorticoids administration in a given patient, reducing the risk of overdosage and of adverse effects due to the treatment, yet preserving the therapeutic effects thereof.

The same method could be used to develop new drugs, even different from glucocorticoids, however able to induce ATMdexa1 expression and therefore bring benefits to the treated patient.

DETAILED DESCRIPTION OF THE INVENTION

Figure 1:
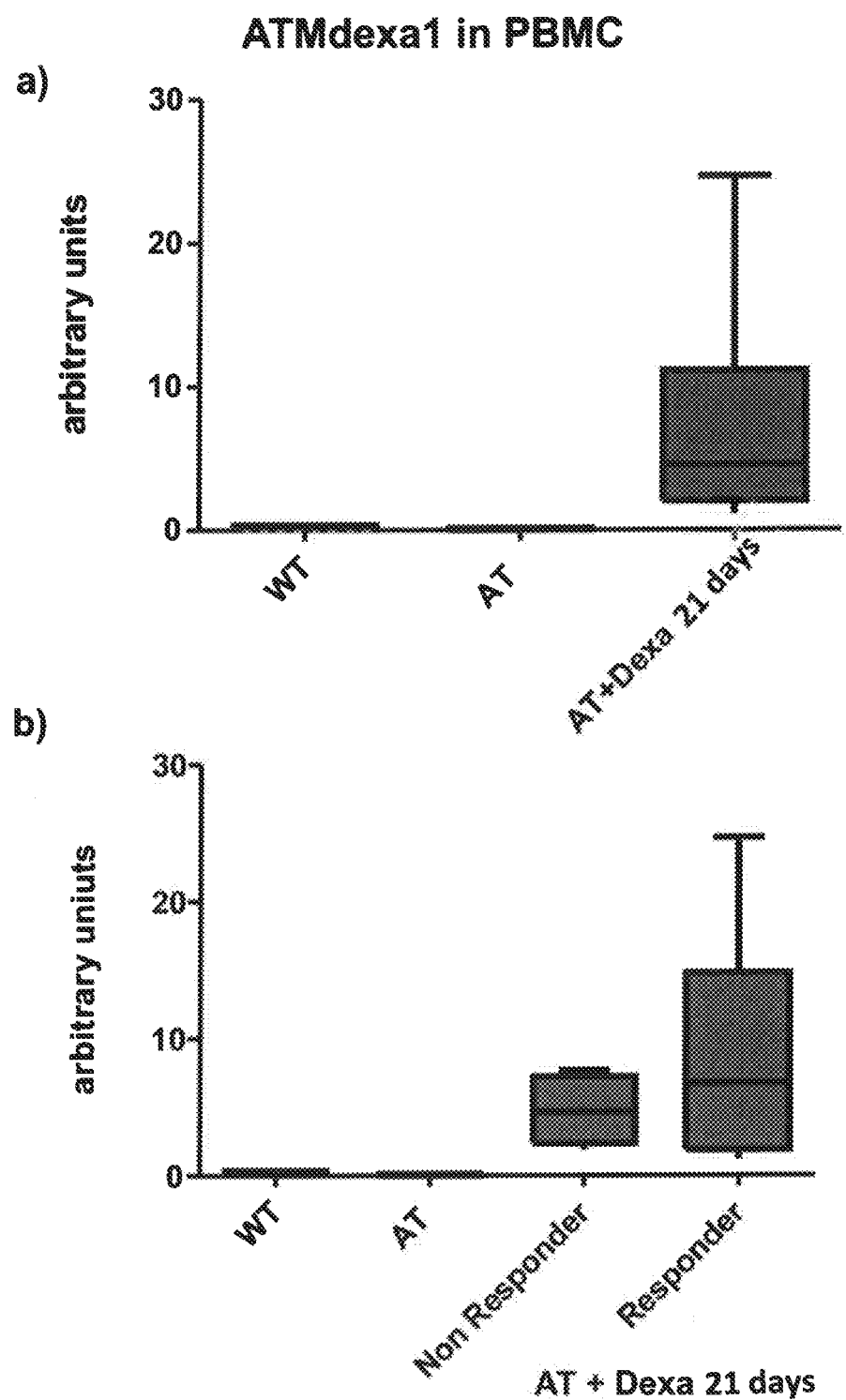
FIG. 1: Qualitative and quantitative identification of ATMdexa1 transcript in blood samples derived from A-T patients treated with ERYDEX. ATMdexa1 expression levels were detected by RT-PCR method with SYBRgreen and compared to the expression levels of untreated A-T patients and untreated WT healthy volunteers (panel a). In a second analysis, the A-T patients treated with ERYDEX were subdivided into two subgroups (responders and non-responders) based on responsiveness to treatment measured with the ICARS scale (Trouillas P, et al. "International Cooperative Ataxia Rating Scale for pharmacological assessment of the cerebellar syndrome. —The Ataxia Neuropharmacology Committee of the World Federation of Neurology". J Neurol Sci. 1997 Feb. 12; 145(2):205-11.) and the related expression levels compared between the two treated subgroups and with the healthy and untreated controls (panel b). As non-responders, in the figure, are considered the patients who, following the treatment, had demonstrated an ICARS value decrease lower than or equal to 10 points, after six months of therapy.

The ATM gene (Ataxia Telangiectasia Mutated gene) was described by Savitsky K, et al. In Science. 1995 Jun. 23; 268(5218):1749-53. The gene, which codifies for a protein kinase of the PI 3-kinase family, is transcribed into 27 different mRNAs and into 20 known variant forms of mRNA due to alternative splicing.

New transcripts of mRNA variants, relevant for the purposes of the present invention, are detectable in the blood of patients affected by Ataxia Telangiectasia subjected to glucocorticoids treatment, and linked to the therapeutic effect on AT of the same glucocorticoids.

Said transcripts are the result of an alternative non-canonical splicing, induced by glucocorticoids, which, by markedly limiting their length with respect to physiological transcripts, removes the mutation sites of the ATM gene, however at least partly preserving its region accountable for the protein kinase enzymatic activity, containing the Phosphatidyl Inositol 3 Kinase domain.

In particular, a previous experimental work, carried out using as exemplary glucocorticoid Dexamethasone sodium phosphate, enabled to identify in vitro, on cell lines of A-T patients, a transcript of about 1582 bp denominated ATMdexa1 (see M. Menotta et al J. Biological Chemistry Vol 287, N. 49 of Nov. 30, 2012.

It has been demonstrated that the administration of dexamethasone derivatives, such as salts different from sodium phosphate, or of glucocorticoids of the same family of dexamethasone, equally known for exerting an improving therapeutic effect on the clinical picture of Ataxia Telangiectasia, act through the same mechanism, inducing the same transcript of mRNA variant or functionally equivalent transcripts.

It has now been observed by the present Inventors that ATMdexa1 synthesis is directly correlated to the treatment with the drug, since neither A-T subjects, nor WT subjects, who did not receive dexamethasone treatment, demonstrated detectable levels of transcript.

For the purposes of the present invention, by the wording "detectable levels of transcript" or "detectable expression values" are meant values that, regardless of detection methodology and operating conditions (e.g., number of cycles or temperature of a PCR) be greater than the average values of the controls (i.e., A-T patients not treated with GC or healthy individuals) of at least 3 times the standard deviation of the reference sample.

Moreover, ATMdexa1 expression is directly and proportionally correlated to clinical effectiveness, it being greater in those patients with a greater decrease of overall symptoms of the disease (i.e., decrease of the ICARS score with entailed ΔICARS increase) and associated with a greater improvement of neurological symptoms (responder patients) compared to patients for which no significant improvements of disease symptoms were observed (non-responder patients). Non-responders are considered the patients who, following the treatment, have demonstrated a decrease of the ICARS value lower than or equal to 10 points, after six months of therapy.

Moreover, it was demonstrated that the expression of genes, such as FKBP5 and DUSP1, known to be more expressed in dexamethasone treatment, does not vary in the two patient groups (responders and non-responders) therefore highlighting the specificity of miniATM as specific biomarker of therapy effectiveness.

Lastly, ATMdexa1 expression was demonstrated greater in the days immediately after medicament infusion and slowly decreases over time, along with the disappearance of the circulating drug, confirming a relationship between Dexamethasone administration, clinical response, and ATMdexa1 expression.

The treatments and patients susceptible of being monitored with the method of the present invention are treatments of AT with administration of glucocorticoids known to positively affect the clinical picture of the disease. Glucocorticoids are selected from the family comprising prednisolone, dexamethasone, betamethasone, deflazacort, derivatives thereof and salt forms thereof, such as phosphate diacid or sodium phosphate, for instance dexamethasone phosphate, dexamethasone sodium phosphate, betamethasone phosphate or sodium phosphate, prednisolone phosphate or sodium phosphate, deflazacort phosphate or sodium phosphate. Evidently, the forms salified with sodium can be replaced by the corresponding and usual salts of group IA or IIA metals without altering the essence of the invention.

In a specific form of treatment monitorable thorugh the method of the invention, the medicament is administered in a form encapsulated within erythrocytes. The encapsulation process is described in Appn. WO2014/181309 (PCT/IB2014/061338) entitled: "Process for the Preparation of Erythrocytes Loaded with One or More Substances of Pharmaceutical Interest and so Obtained Erythrocytes".

The experimental work described in the present application was carried out by using dexamethasone sodium phosphate encapsulated within erythrocytes according to the method described in WO2014/181309.

Various methods, all based on polymerase chain reaction, were contrived and set up for identification and quantification of the expression of the mRNA variant, e.g. of ATMdexa1, in the collected blood sample. All methodologies introduced herein allow relative and/or absolute quantification of messenger RNA in the sample of interest.

By way of example, the amplification is carried out on blood samples or on peripheral mononuclear cells (PBMC), by techniques selected from: PCR, RT-PCR, RT-PCR with an intercalating agent, Taq polymerase-PCR, Molecular Beacon probe method PCR, FRET-probe hybridization, Scorpion probe PCR. The protocols for each technology are described in the experimental section of the present application and are object of the invention.

As quantification method, it was preferably used that of the standard curve set up from a molecule of recombinant plasmid for the sequence of the mRNA transcript (e.g., ATMdexa1) added in known and increasing amounts in DNA samples used as standard to evaluate amplification effectiveness and method linearity. The same serial dilutions of the plasmid/mRNA can be used as PCR positive control and as gold standard for absolute quantification of the target molecule. Alternatively, the assay provides a pair of primers for amplifying, concomitantly with the target, the mRNA of HPRT1, selected as housekeeping gene in the sample of interest. Besides HPRT1, other reference genes were tested (e.g., GAPDH, β2M, etc.) and might be used for the relative quantification of ATMdexa1 thanks to the ΔΔCt or Pfaffel methods.

In accordance with the various technologies, suitable forward and reverse primers were designed and implemented by the present Inventors. The nucleotide sequences of said primers are listed in the sequence listing and in Table 1 below.

According to the technology employed, suitable probes for amplificate detection are also used. The sequences of some of these probes are reported in the sequence listing and in Table 1.

TABLE 1

| Method | Forward Primer 5'-3' | Reverse Primer 5'-3' | Probe 5'-3' | Reporter/ Fluorophore/ Donor | Quencer/ Fluorophore | Quantification |
|---|---|---|---|---|---|---|
| SYBRgreen qRT-PCR | ATCTAGATC GGCATTCA GATTCCA (SEQ ID NO: 1) | GTTTAGTAAT TGGCTGGTCT GC (SEQ ID NO: 33) | none | SYBRgreen | none | Direct |
| 5' Nuclease assay | CGCCTGATT CGAGATCC TGAA (SEQ ID NO: 3) | GTGCCTCAA CACTTCTGA CCAT (SEQ ID NO: 4) | AAACATCTAGAT CGGCATTCAGAT TCCAA (SEQ ID NO: 4) | Cy3 | BHQ2 | |
| 5' Nuclease assay | CGCCTGATT CGAGATCC TGAA (SEQ ID NO: 6) | GTGCCTCAA CACTTCTGA CCAT (SEQ ID NO: 7) | TCTAGATCGGCA TTCAGATTCC (SEQ ID NO: 8) | Cy3 | BHQ2-Plus | |
| Molecular Beacons | AGAATGTCT GAGAATAG CA (SEQ ID NO: 9) | CTGAGTGGC ATCTAAGTT (SEQ ID NO: 34) | GATGGTCAGAAG TGTTGAGG (SEQ ID NO: 11) | 6-FAM | BHQ1 | Molecular Beacon |
| Hybridization/ FRET Probes/ LightCycler® Probes | ATCCTGAAA CAATTAAAC AT (SEQ ID NO: 12) | ATAATATAA GCATCACAA AGT (SEQ ID NO: 35) | TTTACAGAAATA TATTCAGAAAGA AACAGA (SEQ ID NO: 14)/ TGAGAATAGCAA AACCAAATGTAT C (SEQ ID NO: 15) | FAM | LC red 640 | |

Lastly, examples of primers and probes for amplification of known housekeeping genes, used as positive control in the amplification processes according to the invention, are reported in Table 2.

tigations were carried out on blood samples from A-T patients not treated with Dexamethasone drug and volunteer healthy (WT) subjects, used as control. In said samples, ATMdexa1 was never detected (FIG. 1a). Reported results

TABLE 2

| Method | Forward Primer 5'-3' | Reverse Primer 5'-3' | Probe 5'-3' | Reporter/ Fluorophore/ Donor | Quencher/ Fluorophore | Quantification |
|---|---|---|---|---|---|---|
| SYBRgreen qRT-PCR | TATGCTGAG GATTTGGAA AGGGT (SEQ ID NO: 16) | AGAGGGCTA CAATGTGAT GG (SEQ ID NO: 36) | none | SYBRgreen | none | Direct |
| 5' Nuclease assay | GGAAAGGG TGTTTATTC CTCATGGA (SEQ ID NO: 18) | GGCCTCCCA TCTCCTTCAT C (SEQ ID NO: 19) | TATGGACAGGACT GAACGTCTTGC (SEQ ID NO: 20) | JOE | BHQ1 | |
| 5' Nuclease assay | GGATTTGG AAAGGGTG TTTATTCC (SEQ ID NO: 21) | GGCCTCCCA TCTCCTTCAT C (SEQ ID NO: 22) | TGGACTAATTATG GACAGGACTGA (SEQ ID NO: 23) | JOE | BHQ1-Plus | |
| 5' Nuclease assay | TATGCTGAG GATTTGGAA AGGGT (SEQ ID NO: 24) | AGAGGGCTA CAATGTGAT GG (SEQ ID NO: 37) | TATGGACAGGACT GAACGTCTTGC (SEQ ID NO: 20) | JOE | BHQ1 | |
| Molecular Beacons | TCGTGATTA GTGATGAT GA (SEQ ID NO: 26) | GTTCAGTCCT GTCCATAA (SEQ ID NO: 38) | TACCTAATCATTAT GCTGAGGATT (SEQ ID NO: 28) | HEX | BHQ1 | |
| Hybridization/ FRET Probes/ LightCycler® Probes | GGCTATAA ATTCTTTGC T (SEQ ID NO: 29) | ACCAATTACT TTTATGTCC (SEQ ID NO: 39) | AGATCCATTCCTA TGACTGTAGATT (SEQ ID NO: 31)/ CAGACTGAAGAGC TATTGTAATGAC (SEQ ID NO: 32) | FAM | LC red 640 | |

EXPERIMENTAL SECTION

The following section reports, by way of example, an experimental work performed under the IEDAT clinical study, using dexamethasone as representative sample of glucocorticoid medicaments.

In Vivo Experimentation

Following approval of the ethical committees in charge, and with approval by the patients or their legal guardians if minors, blood samples of 10 out of 22 patients enrolled in the IEDAT clinical study were obtained. Blood collection was carried out at the end of the treatment, precisely at Day 21 from the sixth and latter infusion of intra-erhytrocitary dexamethasone (ERYDEX®) provided by the clinical study. The blood sample was also collected in specially provided tubes (vacutainers) containing a stabilizing solution adapted to preserve RNA for the subsequent extraction. In short, the extracted RNA was back transcribed into the corresponding cDNA and subjected to analyses aimed at measuring ATMdexa1 expression. For this purpose, a Real Time PCR assay was set up for qualitative and quantitative analysis, able to specifically identify the new mRNA molecule first described in lymphoblastoid cells. Thanks to said assay, ATMdexa1 was identified in all 10 available samples. The same inves- suggest that the induction of ATMdexa1 isoform seems to be strictly dependent on the treatment with the drug.

Figure 2:
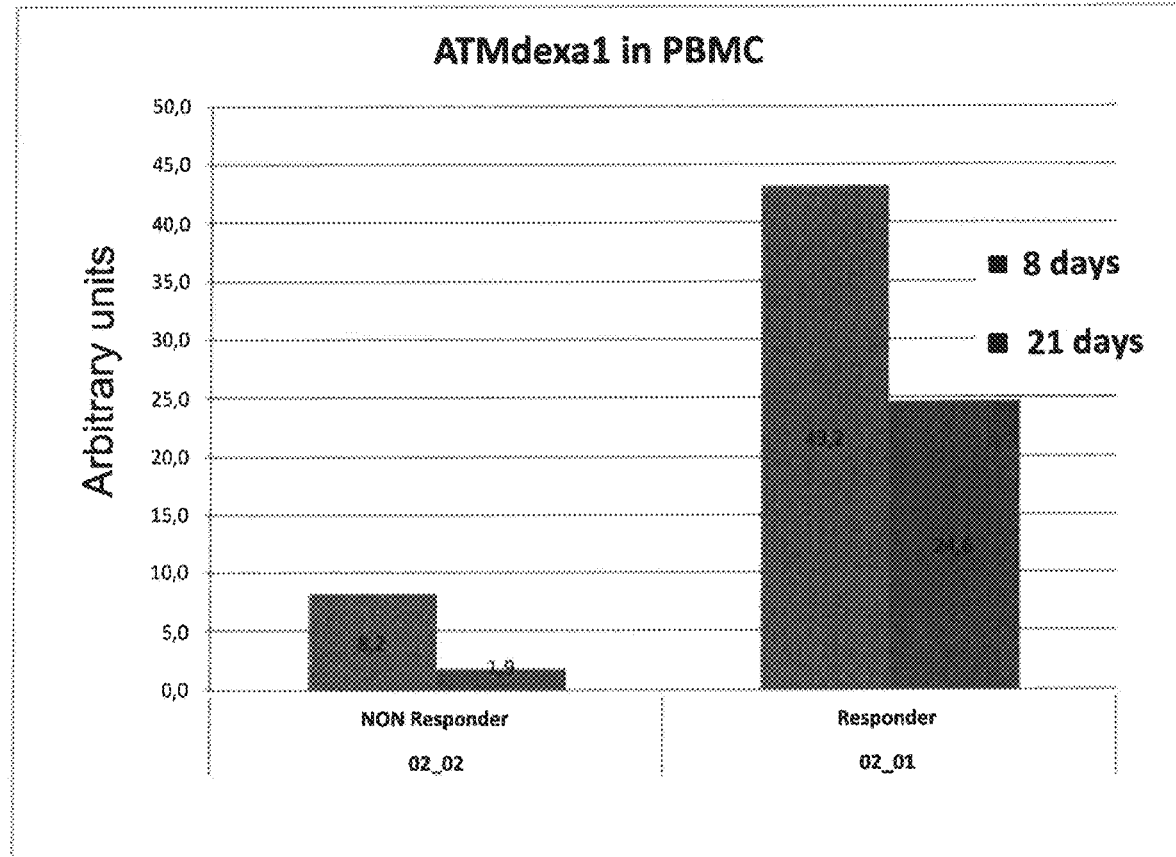
FIG. 2: ATMdexa1 quantification at different times from treatment. For a responder patient and a non-responder patient, expression levels were evaluated at +8 and +21 days from ERYDEX administration.

ERYDEX efficacy on neurological symptoms of A-T patients, evaluated under the study by ICARS scale, revealed that a greater improvement was associated to a greater encapsulation and, therefore, to a greater administration of drug [11]. For this reason, patients were clustered in responders (or "loaders") and non-responders (or "non-loaders"). To correlate dexa efficacy with ATMdexa1 induction, a subanalysis was performed by subdividing the samples from the patients into two groups. As shown in FIG. 1b, responder A-T patients (samples) exhibit greater ATMdexa1 expression compared to those from non-responder patients, suggesting that indeed ATMdexa1 expression seems to be directly correlated to, or at least contribute to, dexa efficacy. Lastly, blood samples were analyzed, from a single patient of both groups, collected at different times from ERYDEX infusion, specifically at +8 and +21 days from administration. In this case as well, responder patients demonstrated expression levels greater than non-responders at both times. However, it was surprisingly observed (by comparing intra-patient levels in both cases) that the ATMdexa1 transcript is expressed at greater levels at the +8 day time than at the +21 day time (FIG. 2). This is consistent with the gradual waning of dexa effect over time from the treatment, a fact stressing the need to resort to repeated administrations in order to keep the drug effectiveness active.

Figure 5A:
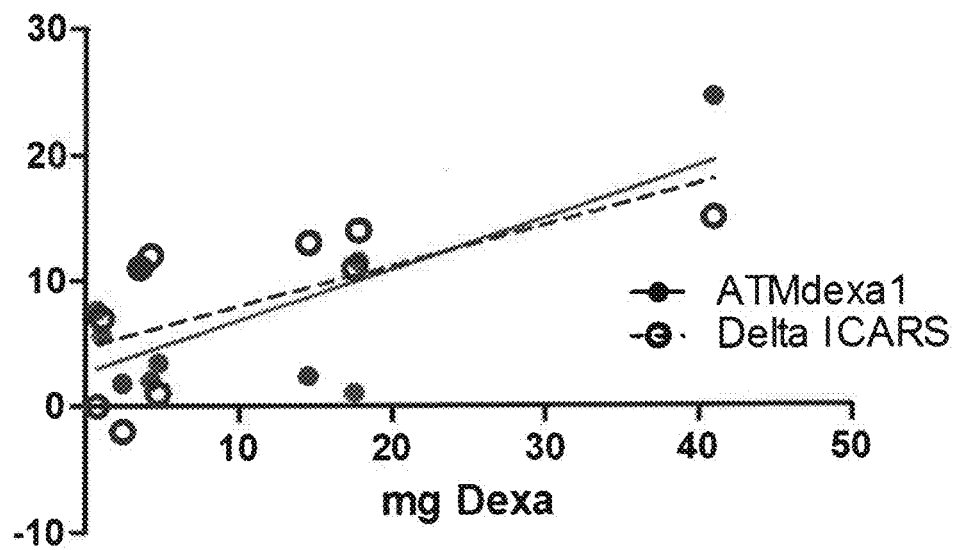
FIG. 5: Analysis of the linear relationship existing between miniATM expression levels and ICARS variation depending on the administered amount of dexamethasone (Dexa) (Figure a). Confirmation of data related to responsiveness to treatment with ERYDEX and miniATM expression levels between responders and non-responders, and respective ICARS values (Figure b).
Figure 5B:
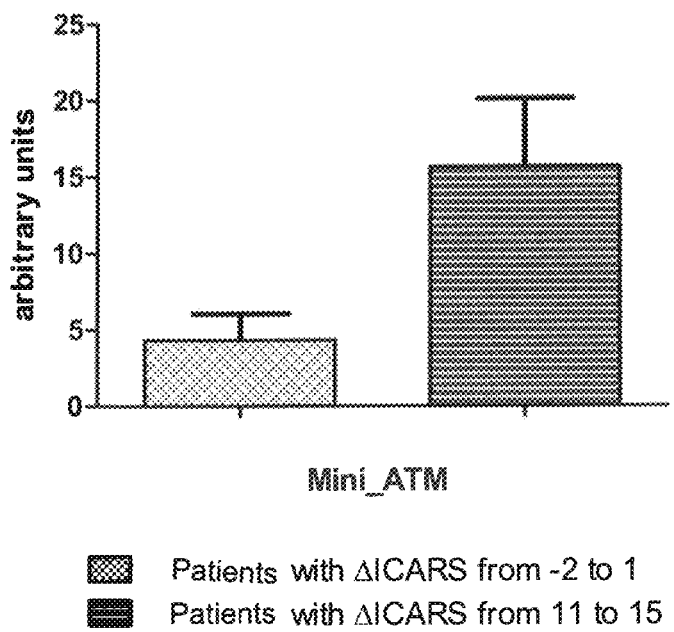
Figure 6:
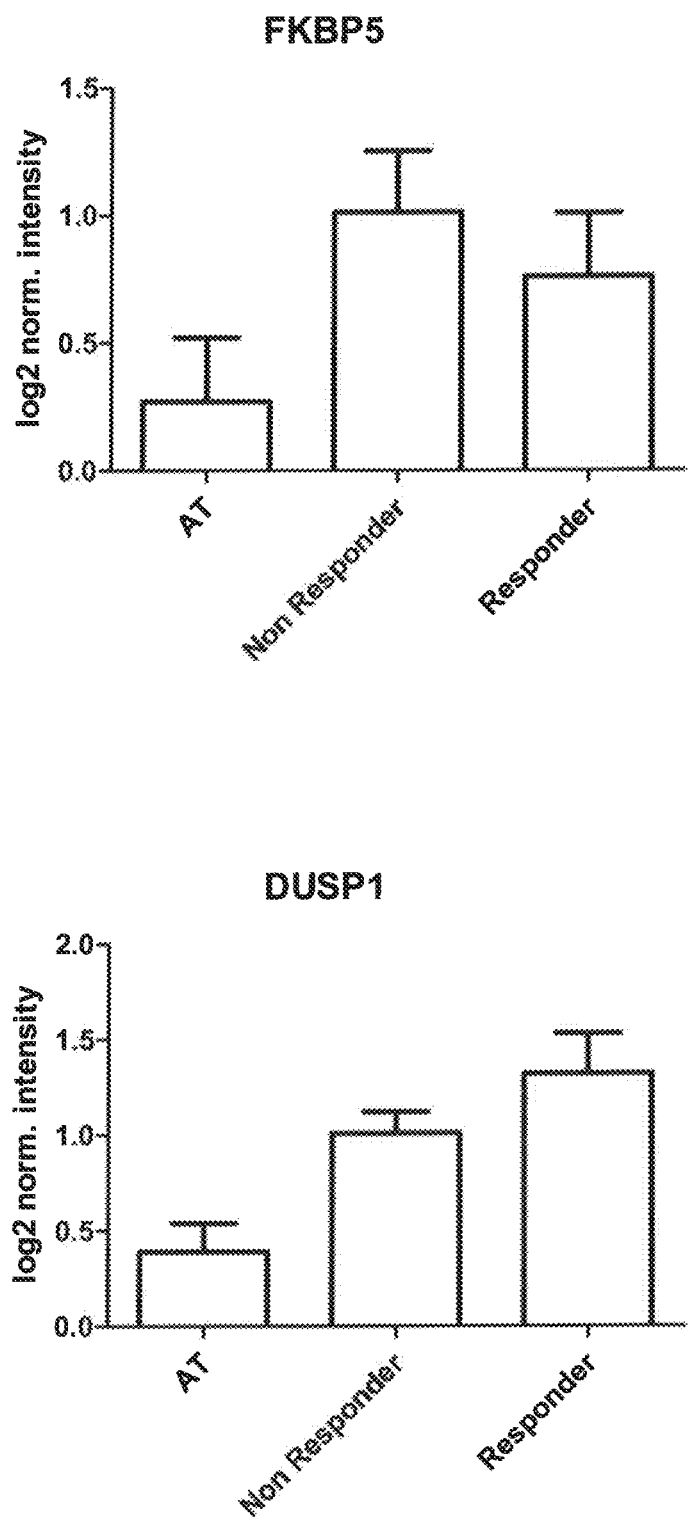
FIG. 6: Assessment of expression of FKBP5 and DUSP1 genes, whose transcription is induced by dexamethasone administration, in responder and non-responder patients treated with Erydex.

In a subsequent experiment, in which patients were enrolled similarly to what described above, a directly proportional relationship was observed between miniATM expression and ICARS variation depending on the amount of drug (dexamethasone) administered (FIG. 5 a). In particular, the correlation between miniATM expression and amount of drug (dexamethasone) administered is of linear type. Moreover, it was confirmed that an increase of miniATM expression correlates with a greater improvement of neurological symptoms, i.e. decrease of ICARS scores and entailed ΔICARS increase. (FIG. 5 b).

Lastly, an evaluation of FKBP5 and DUSP1 genes expression in the same samples used for miniATM determination highlighted that, while glucocorticoids treatment always increases the expression of such genes, the expression level does not change significantly in the two groups of patients (responders and non-responders). This observation highlights the specificity of miniATM expression as specific biomarker of therapy efficacy.

To sum up, the new ATMdexa1 transcript recently identified in ATM$^{-/-}$ lymphoblastoid cell lines [14], was first identified in vivo, in particular, in PMBCs of A-T patients treated with ERYDEX. ATMdexa1 synthesis is directly correlated to treatment with the drug, as neither A-T subjects, nor WT subjects who did not receive dexamethasone demonstrated detectable levels of transcript. Moreover, ATMdexa1 expression is directly correlated with clinical efficacy, it being greater in those patients with greater decrease of ICARS score and associated with a greater improvement of neurological symptoms. Lastly, ATMdexa1 expression proved greater in the days immediately subsequent to ERYDEX infusion and slowly decreases over time, in parallel with the disappearance of circulating drug, confirming an association between Dexamethasone administration, clinical response and ATMdexa1 expression.

Experimental Protocol for ATMdexa1 mRNA Identification and Quantification in PBMCs of A-T Patients Treated with Dexamethasone 1) Samples Collection:

3 ml of blood were collected from A-T patients and healthy volunteers directly in vacutainer Tempus Blood RNA tubes (Applied Biosystems), containing a lysing solution and a stabilizing reagent that assures RNA preservation until subsequent extraction. Immediately after withdrawal, samples were frozen and could be kept at −20° C. for several months. Shipment from hospital centers to the Inventors' laboratory was carried out at the same temperature to avoid sample defrosting and deterioration.

2) Total RNA Extraction and Complementary DNA Synthesis:

Blood samples were processed for total RNA extraction by Tempus spin RNA isolation kit (Applied Biosystems) as reported in the manufacturer's instructions.

A cleanup process was made to follow a previous purification by QIAGEN RNA extraction kit for a complete elimination of contaminating DNA. The average yield was about 8.5 micrograms of pure total RNA for each sample, consisting at the start of 3 ml of whole blood. Then, 500 ng RNA from each sample were employed for retro-transcription reaction into the corresponding complementary DNA (cDNA), catalyzed by the enzyme SMARTScribe Reverse Transcriptase (Clontech) in the presence of oligodT or Random hexamers or both, to prime the reaction. cDNAs synthesis was conducted as reported in the protocol illustrated by the manufacturer.

Exogenous, not conserved RNA molecule, obtained from a species other than *Homo sapiens* (e.g., bacterial or plant mRNA), was added prior to RNA extraction and cDNA synthesis procedures, as internal control, so as to be able to verify extraction, synthesis and subsequent amplification efficiencies. More preferably, the molecule used as standard may be added directly into the stabilizing solution contained into the vacutainer.

3) PCR Assay for ATMdexa1 Quantification in the Samples:

Several methods, all based on polymerase chain reaction (PCR), have been contrived and set up for ATMdexa1 identification and quantification in the collected blood sample; some of them are described in detail hereinafter and therefore claimed as invention. All the methodologies introduced here permit the relative and/or absolute quantification of the ATMdexa1 messenger RNA in the sample of interest.

a) The first method claimed envisages the use of an intercalating agent, like, e.g., SYBRgreen or any other fluorophore having intercalating action, into the double strand (ds) of the DNA. Such a technology is based on the specific amplification of a cDNA family by quantitative real-time PCR in the presence of the intercalating agent that intercalates into the double strand of the increasing DNA to monitor amplicon synthesis. Specifically, for their experiments the Inventor used SYBR Premix Ex Taq (Tli RNaseH Plus) by Takara, containing the enzyme Taq polymerase and SYBRgreen in a suitable buffer system. An additional amount of $MgCl_2$ was added to the reaction mixture to reach the optimal final concentration of 3.5 mM, as well as a pair of specific primers at a final concentration of 300 nM. The oligonucleotide pair was designed in silico to recognize selectively the DNA complementary to the ATMdexa1 transcript (ATMdexa1 cDNA) to the detriment of native mRNA (Tables 1 and 2). In the example proposed herein, raw fluorescence, measured in real time in the samples under amplification, will be strictly dependent on the ATMdexa1 RNA quantity present in the sample of origin, and will employ a number of amplification cycles inversely proportional to the initial RNA quantity, to reach the threshold level of fluorescence. The thermal profile optimized to obtain a specific and linear amplification of ATMdexa1 was set in 40 cycles of denaturation (for 10 sec at 94° C.), annealing (for 20 sec at 65° C.) and extension at 72° C. for 36 seconds. As method for quantification, it was used that of a standard curve assembled from a molecule of plasmid recombinant for the ATMdexa1 sequence added in known and increasing quantities in DNA samples used as standard to assess amplification efficiency and linearity of the method. The same serial dilutions of ATMdexa1 plasmid can be used as PCR positive control and as gold standard for absolute quantification of the target molecule. Alternatively, the assay envisages a pair of primers to amplify in the sample of interest, concomitantly with the target, the HPRT1 mRNA selected as housekeeping gene. Besides HPRT1, other reference genes were tested (e.g., GAPDH, β2M, etc.) and might be used for the relative quantification of ATMdexa1 thanks to the ΔΔCt or Pfaffel methods.

Figure 3A:
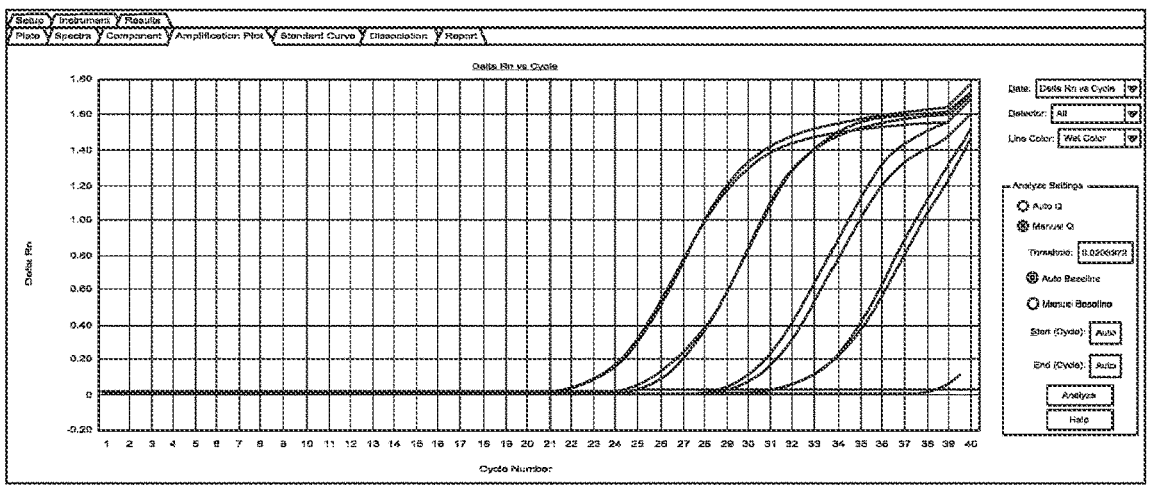
FIG. 3: Exemplary standard curve of ATMdexa1 amplification by RT-PCR method and SYBRgreen. Amplification (panel a), dissociation (panel b) and linearity (panel c) curves were obtained by amplifying serial dilutions of a suitable recombinant plasmid for ATMdexa1.
Figure 3B:
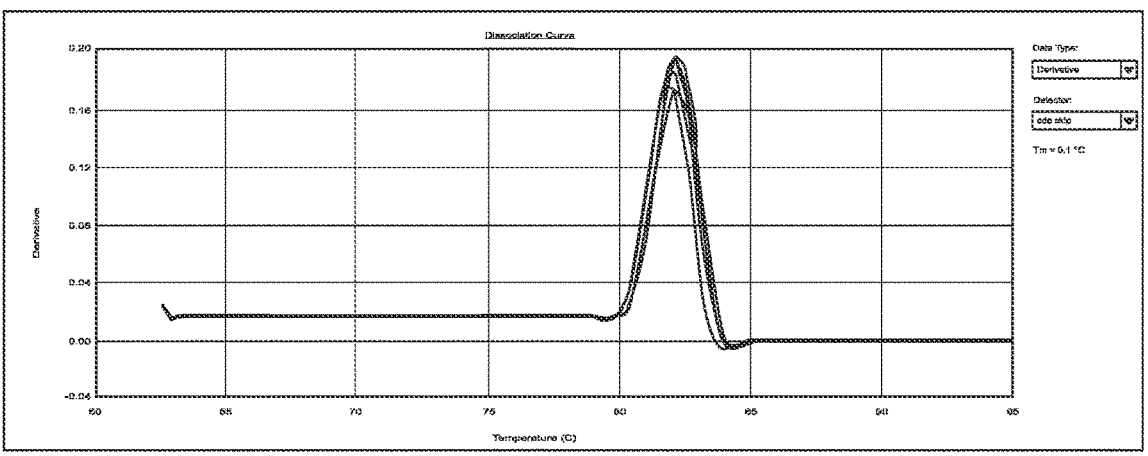
Figure 3C:
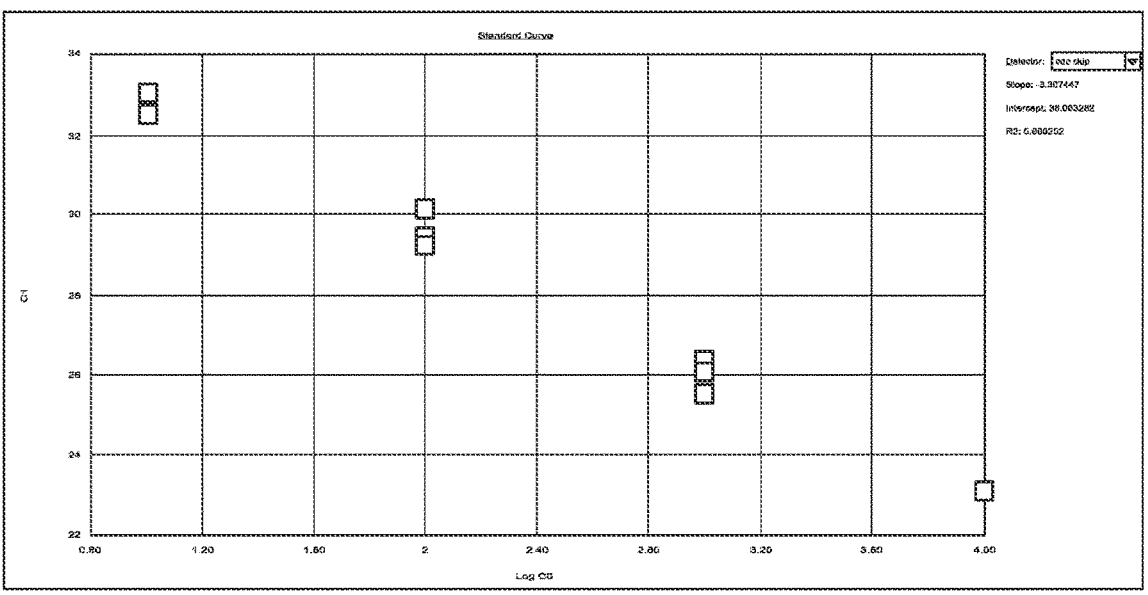

The experimental results, given in the description of the invention, were obtained by means of the assay described in this section. Method validation envisaged the setting up of a standard curve as described above. The related amplification (FIG. 3, panel A), dissociation (FIG. 3, panel B) and linearity (FIG. 3, panel C) curves are reported in FIG. 3, which demonstrates a specific, linear and univocal amplification of ATMdexa1. The extrapolated linearity line has a slope of −3.30 (corresponding to an amplification efficiency of 100%) and an $R^2$ of 0.99.

Figure 4A:
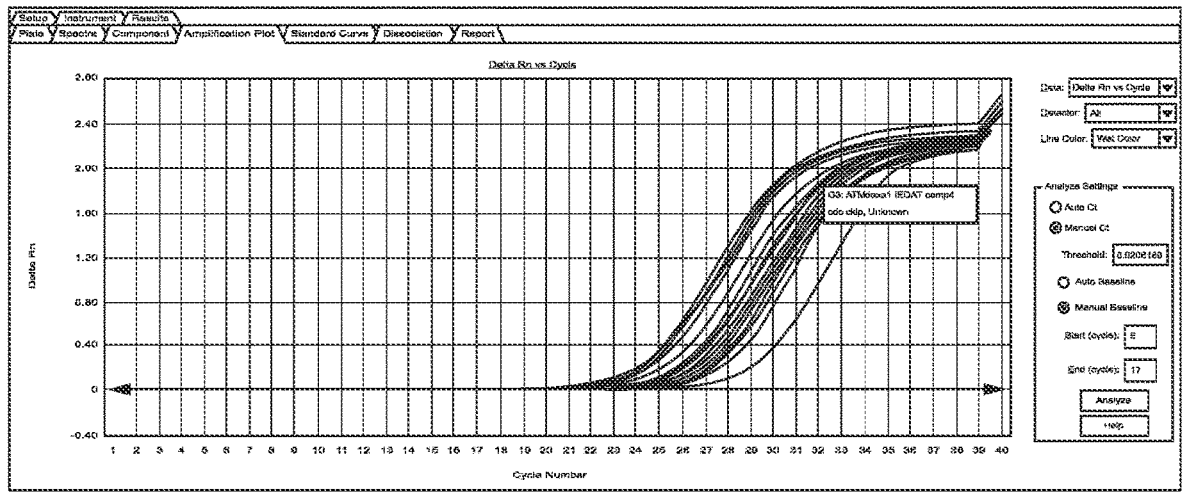
FIG. 4: ATMdexa1 amplification (panel a) and dissociation (panel b) curves in samples of A-T patients treated with ERYDEX.
Figure 4B:
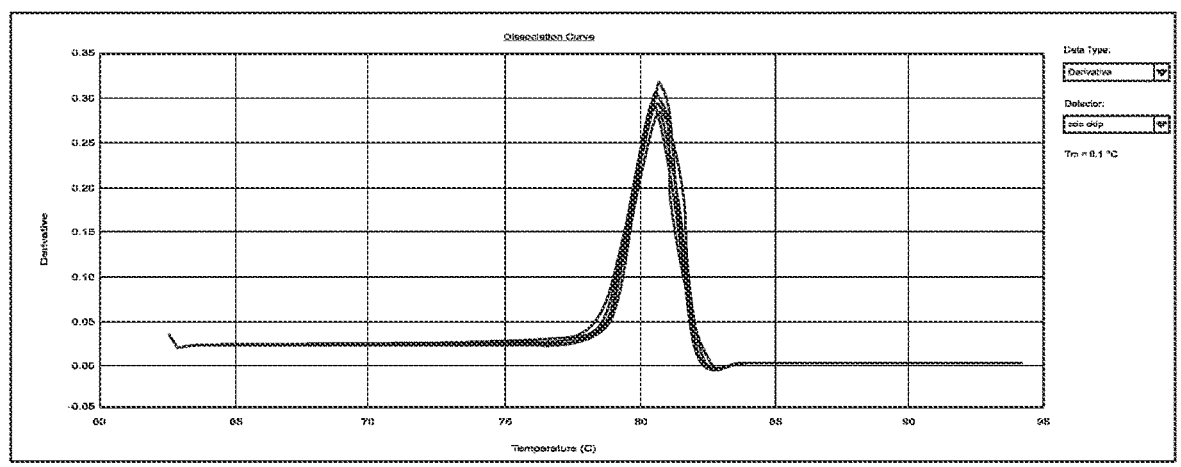

Samples of interest, from A-T patients subjected to dexa treatment, were amplified under the same conditions and compared with those of untreated A-T patients and healthy volunteers. Specific amplification was obtained in all investigation samples, as shown in FIG. 4, whereas no amplification was detected in the control samples. Threshold cycles (Ct) derived for positive samples were used for calculation of the relative amounts of ATMdexa1 mRNA subtracting the related threshold Ct of the housekeeping HPRT1.

b) The second method exemplified is based on 5'-Nuclease Assay, exploiting the 5'-esonuclease activity of Taq polymerase enzyme. Besides the pair of specific primers, a likewise specific DNA probe is used, which anneals on the newly synthesized amplicon and is hydrolyzed by polymerase during chain extension. The probe bears, bound to the 3'- and 5'-ends, respectively a quencher (BHQ or BHQ-Plus quencher) and a reporter fluorophore, where the former inhibits emission of the latter. Hydrolysis of the probe by the polymerase causes detachment and separation of the quencher, with consequent fluorescence emission. The reaction was performed on the samples of the Inventors by using the HOT-RESCUE REAL TIME PCR FP Kit (Diatheva). For the ATMdexa1 target a specific probe with Cy3 as reporter fluorophore was designed, while for the housekeeping HPRT1 a specific probe with JOE as fluorophore was designed, so as to have signals specific for the target gene and the reference gene and be able to carry out both reactions in multiplex PCR. The concentration of the two pairs of primers (Table 1 and 2) was optimized to 500 nM, while the probe concentration was 100 nM. The thermal profile was set on 50 denaturation cycles of 15 sec at 94° C., followed by an annealing/extension step at 60° C. for 60 seconds. In this case as well, the quantification of ATMdexa1 can be carried out either in relative manner (with respect to the reference gene) or in absolute manner, as described in the previous example.

c) ATMdexa1 can be quantified by a series of other assays, all based on PCR technology. For example, probes to be used in the Molecular Beacons method were designed by the Inventors. In this application, the amplification is performed in the presence of Molecular beacon probes that are labeled at the 5' terminus with a fluorescent reporter dye (FAM for ATMdexa1 and HEX for HPRT1) and at the 3' terminus with a quencher (BHQ1, Tables 1 and 2). During the annealing step, the primers and probes hybridize to the respective sequence of complementary DNA. Hybridization of probes, in particular, causes their "opening" and the entailed separation of the fluorophore and quencher; the quencher therefore can no longer absorb the energy emitted by the reporter fluorophore.

d) Another example of method proposed is based on a Hybridization/FRET probe, consisting in the use of two labeled probes: the first one on the 3' end with a donor fluorophore (FAM), whereas the second one on the 5' end with an acceptor fluorophore (LC red 640).

e) Finally, the PCR assay may be set up from Scorpion technology probes. The sequences of all the primers pairs and of all the probes proposed in the above-mentioned examples, for amplification and successive quantification of ATMdex1 in the biological samples, are reported in tables 1 and 2. All methods mentioned, as well as any other method set up as variant on the theme of the previous ones, envisaging the quantification of ATMdexa1 by means of polymerase chain reaction (for example, Digital PCR) fall within the scope of the present invention.

REFERENCES

1. Broccoletti T, Del G E, Amorosi S, Russo I, Di B M et al. Steroid-induced improvement of neurological signs in ataxia-telangiectasia patients. Eur J Neurol 2008, 15:223-228.
2. Buoni S, Zannolli R, Sorrentino L, and Fois A. Betamethasone and is improvement of neurological symptoms in ataxia-telangiectasia. Arch Neurol 2006, 63:1479-1482.
3. Russo I, Cosentino C, Del G E, Broccoletti T, Amorosi S et al. In ataxia-teleangiectasia betamethasone response is inversely correlated to cerebellar atrophy and directly to antioxidative capacity. Eur J Neurol 2009, 16:755-759.
4. Broccoletti T, Del G E, Cirillo E, Vigliano I, Giardino G et al. Efficacy of very-low-dose betamethasone on neurological symptoms in ataxia-telangiectasia. Eur J Neurol 2011, 18:564-570.
5. Gatti R A and Perlman S. A proposed bailout for A-T patients? Eur J Neurol 2009, 16:653-655.
6. Biagiotti S, Paoletti M F, Fraternale A, Rossi L, and Magnani M. Drug delivery by red blood cells. IUBMB Life 2011, 63:621-631.
7. Bossa F, Latiano A, Rossi L, Magnani M, Palmieri 0 et al. Erythrocyte-mediated delivery of dexamethasone in patients with mild-to-moderate ulcerative colitis, refractory to mesalamine: a randomized, controlled study. Am J Gastroenterol 2008, 103:2509-2516.
8. Castro M, Rossi L, Papadatou B, Bracci F, Knafelz D et al. Long-term treatment with autologous red blood cells loaded with dexamethasone 21-phosphate in pediatric patients affected by steroid-dependent Crohn disease. J Pediatr Gastroenterol Nutr 2007, 44:423-426.
9. Pierige F, Serafini S, Rossi L, and Magnani M. Cell-based drug delivery. Adv Drug Deliv Rev 2008, 60:286-295.
10. Rossi L, Serafini S, Cenerini L, Picardi F, Bigi L et al. Erythrocyte-mediated delivery of dexamethasone in patients with chronic obstructive pulmonary disease. Biotechnol Appl Biochem 2001, 33:85-89.
11. Chessa L, Leuzzi V, Plebani A, Soresina A, Micheli R et al. Intra-erythrocyte infusion of dexamethasone reduces neurological symptoms in ataxia teleangiectasia patients: results of a phase 2 trial. Orphanet J Rare Dis 2014, 9:5.

The invention claimed is:

1. A method for evaluating glucocordicoid (GC) treatment response in a patient affected by Ataxia Telangiectasia, comprising
   a) amplifying an ATMdexa1 nucleotide sequence in blood from said patient to obtain ATMdexa1 nucleotide expression values with primer pairs:
   SEQ ID NO: 1/SEQ ID NO: 33;
   SEQ ID NO: 3/SEQ ID NO: 4,
   SEQ ID NO: 6/SEQ ID NO: 7,
   SEQ ID NO: 9/SEQ ID NO: 34; or
   SEQ ID NO: 12/SEQ ID NO: 35,
   b) evaluating the ATMdexa1 nucleotide expression values, and
   c) administering GC treatment when detectable nucleotide expression values of ATMdexa1 are obtained and reducing and/or discontinuing GC treatment when no detectable expression values of ATMdexa1 are obtained.

2. The method according to claim 1, wherein the glucocorticoid is prednisolone, dexamethasone, betamethasone, deflazacort, or pharmaceutically acceptable salts or esters thereof or mixtures thereof.

3. The method according to claim 1, wherein the glucocorticoid is prednisolone phosphate, dexamethasone phosphate, betamethasone phosphate, betamethasone phosphate, deflazacort phosphate or sodium salts thereof.

4. The method according to claim 1, wherein the ATMdexa1 expression value is normalized versus the expression of a housekeeping gene.

5. The method according to claim 1, wherein the amplifying is performed by PCR, RT-PCR, RT-PCR with an intercalating agent, Taq polymerase-PCR, Molecular Beacon probe method PCR, FRET-probe hybridization, or Scorpion probe PCR.

6. The method according to claim 5, wherein the amplifying is carried out using a probe of SEQ ID NO:5, SEQ ID NO:8, SEQ ID NO:11, SEQ ID NO:14, or SEQ ID NO:15.

7. The method according to claim 1, wherein the glucocorticoid is a glucocorticoid encapsulated within erythrocytes.

8. The method according to claim 7, wherein the glucocorticoid is dexamethasone phosphate mono or disodium.

9. A method for treating patients affected by Ataxia Telangiectasia, comprising
   a) administering an amount of glucocorticoid to said patient;
   b) qualitatively and/or quantitatively identifying expression of ATMdexa1 in blood of said patient, by amplifying said ATMdexa1 nucleic acid with primer pairs:
   SEQ ID NO: 1/SEQ ID NO: 33;
   SEQ ID NO: 3/SEQ ID NO: 4,
   SEQ ID NO: 6/SEQ ID NO: 7,
   SEQ ID NO: 9/SEQ ID NO:34; or
   SEQ ID NO: 12/SEQ ID NO: 35, and
   c) reducing glucocorticoid treatment if there are no detectable expression values for ATMdexa1, or continuing glucocorticoid treatment if there are detectable expression values for ATMdexa1, wherein detectable expression values of ATMdexa1 indicate a positive response to treatment.

10. The method according to claim 9, wherein the glucocorticoid is prednisolone, dexamethasone, betamethasone, deflazacort or pharmaceutically acceptable salts or esters thereof, preferably phosphate, or mixtures thereof.

11. The method according to claim 9, wherein the glucocorticoid is a glucocorticoid encapsulated within erythrocytes.

12. The method according to claim 9, wherein the glucocorticoid is dexamethasone phosphate mono or disodium.

13. The method according to claim 9, wherein the glucocorticoid is dexamethasone.

* * * * *

SEQUENCE LISTING

<160> NUMBER OF SEQ ID NOS: 39

<210> SEQ ID NO 1
<211> LENGTH: 24
<212> TYPE: DNA
<213> ORGANISM: Artificial Sequence
<220> FEATURE:
<221> NAME/KEY: source

```
<222> LOCATION: 1..24
<223> OTHER INFORMATION: /mol_type="unassigned DNA"
      /note="primer forward"
      /organism="Artificial Sequence"

<400> SEQUENCE: 1
atctagatcg gcattcagat tcca                                          24

<210> SEQ ID NO 2
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="primer reverse"
      /organism="Artificial Sequence"

<400> SEQUENCE: 2
gcagaccagc caattactaa ac                                            22

<210> SEQ ID NO 3
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="primer forward"
      /organism="Artificial Sequence"

<400> SEQUENCE: 3
cgcctgattc gagatcctga a                                             21

<210> SEQ ID NO 4
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="primer reverse"
      /organism="Artificial Sequence"

<400> SEQUENCE: 4
gtgcctcaac acttctgacc at                                            22

<210> SEQ ID NO 5
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="probe"
      /organism="Artificial Sequence"

<400> SEQUENCE: 5
aaacatctag atcggcattc agattccaa                                     29

<210> SEQ ID NO 6
<211> LENGTH: 21
<212> TYPE: DNA
<213> ORGANISM: Artificial Sequence
<220> FEATURE:
```

```
<221> NAME/KEY: source
<222> LOCATION: 1..21
<223> OTHER INFORMATION: /mol_type="unassigned DNA"
      /note="primer forward"
      /organism="Artificial Sequence"

<400> SEQUENCE: 6
cgcctgattc gagatcctga a                                              21

<210> SEQ ID NO 7
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="primer reverse"
      /organism="Artificial Sequence"

<400> SEQUENCE: 7
gtgcctcaac acttctgacc at                                             22

<210> SEQ ID NO 8
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="probe"
      /organism="Artificial Sequence"

<400> SEQUENCE: 8
tctagatcgg cattcagatt cc                                             22

<210> SEQ ID NO 9
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="primer forward"
      /organism="Artificial Sequence"

<400> SEQUENCE: 9
agaatgtctg agaatagca                                                 19

<210> SEQ ID NO 10
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="primer reverse"
      /organism="Artificial Sequence"

<400> SEQUENCE: 10
aacttagatg ccactcag                                                  18

<210> SEQ ID NO 11
<211> LENGTH: 20
<212> TYPE: DNA
<213> ORGANISM: Artificial Sequence
```

```
<220> FEATURE:
<221> NAME/KEY: source
<222> LOCATION: 1..20
<223> OTHER INFORMATION: /mol_type="unassigned DNA"
      /note="probe"
      /organism="Artificial Sequence"

<400> SEQUENCE: 11
gatggtcaga agtgttgagg                                          20

<210> SEQ ID NO 12
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="primer reverse"
      /organism="Artificial Sequence"

<400> SEQUENCE: 12
atcctgaaac aattaaacat                                          20

<210> SEQ ID NO 13
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="primer reverse"
      /organism="Artificial Sequence"

<400> SEQUENCE: 13
actttgtgat gcttatatta t                                        21

<210> SEQ ID NO 14
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="probe"
      /organism="Artificial Sequence"

<400> SEQUENCE: 14
tttacagaaa tatattcaga aagaaacaga                               30

<210> SEQ ID NO 15
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="probe"
      /organism="Artificial Sequence"

<400> SEQUENCE: 15
tgagaatagc aaaaccaaat gtatc                                    25

<210> SEQ ID NO 16
<211> LENGTH: 23
<212> TYPE: DNA
```

```
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="primer forward"
      /organism="Artificial Sequence"

<400> SEQUENCE: 16
tatgctgagg atttggaaag ggt                                          23

<210> SEQ ID NO 17
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="primer reverse"
      /organism="Artificial Sequence"

<400> SEQUENCE: 17
ccatcacatt gtagccctct                                              20

<210> SEQ ID NO 18
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="primer forward"
      /organism="Artificial Sequence"

<400> SEQUENCE: 18
ggaaagggtg tttattcctc atgga                                        25

<210> SEQ ID NO 19
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="primer reverse"
      /organism="Artificial Sequence"

<400> SEQUENCE: 19
ggcctcccat ctccttcatc                                              20

<210> SEQ ID NO 20
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="probe"
      /organism="Artificial Sequence"

<400> SEQUENCE: 20
tatggacagg actgaacgtc ttgc                                         24

<210> SEQ ID NO 21
<211> LENGTH: 24
```

```
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="primer forward"
      /organism="Artificial Sequence"

<400> SEQUENCE: 21
ggatttggaa agggtgttta ttcc                                        24

<210> SEQ ID NO 22
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="primer reverse"
      /organism="Artificial Sequence"

<400> SEQUENCE: 22
ggcctcccat ctccttcatc                                             20

<210> SEQ ID NO 23
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="probe"
      /organism="Artificial Sequence"

<400> SEQUENCE: 23
tggactaatt atggacagga ctga                                        24

<210> SEQ ID NO 24
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="primer forward"
      /organism="Artificial Sequence"

<400> SEQUENCE: 24
tatgctgagg atttggaaag ggt                                         23

<210> SEQ ID NO 25
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="primer reverve"
      /organism="Artificial Sequence"

<400> SEQUENCE: 25
ccatcacatt gtagccctct                                             20

<210> SEQ ID NO 26
```

```
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="primer forward"
      /organism="Artificial Sequence"

<400> SEQUENCE: 26
tcgtgattag tgatgatga                                              19

<210> SEQ ID NO 27
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="primer reverse"
      /organism="Artificial Sequence"

<400> SEQUENCE: 27
ttatggacag gactgaac                                               18

<210> SEQ ID NO 28
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="probe"
      /organism="Artificial Sequence"

<400> SEQUENCE: 28
tacctaatca ttatgctgag gatt                                        24

<210> SEQ ID NO 29
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="primer forward"
      /organism="Artificial Sequence"

<400> SEQUENCE: 29
ggctataaat tctttgct                                               18

<210> SEQ ID NO 30
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="primer reverse"
      /organism="Artificial Sequence"

<400> SEQUENCE: 30
ggacataaaa gtaattggt                                              19
```

```
<210> SEQ ID NO 31
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="probe"
      /organism="Artificial Sequence"

<400> SEQUENCE: 31
agatccattc ctatgactgt agatt                                         25

<210> SEQ ID NO 32
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="probe"
      /organism="Artificial Sequence"

<400> SEQUENCE: 32
cagactgaag agctattgta atgac                                         25

<210> SEQ ID NO 33
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="primer reverse"
      /organism="Artificial Sequence"

<400> SEQUENCE: 33
gtttagtaat tggctggtct gc                                            22

<210> SEQ ID NO 34
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="primer reverse"
      /organism="Artificial Sequence"

<400> SEQUENCE: 34
ctgagtggca tctaagtt                                                 18

<210> SEQ ID NO 35
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="primer reverse"
      /organism="Artificial Sequence"

<400> SEQUENCE: 35
ataatataag catcacaaag t                                             21
```

```
<210> SEQ ID NO 36
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="primer reverse"
      /organism="Artificial Sequence"

<400> SEQUENCE: 36
agagggctac aatgtgatgg                                              20

<210> SEQ ID NO 37
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="primer reverse"
      /organism="Artificial Sequence"

<400> SEQUENCE: 37
agagggctac aatgtgatgg                                              20

<210> SEQ ID NO 38
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="primer reverse"
      /organism="Artificial Sequence"

<400> SEQUENCE: 38
gttcagtcct gtccataa                                                18

<210> SEQ ID NO 39
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="primer reverse"
      /organism="Artificial Sequence"

<400> SEQUENCE: 39
accaattact tttatgtcc                                               19
```